(12) United States Patent
Landis-Lowell

(10) Patent No.: US 6,419,390 B1
(45) Date of Patent: Jul. 16, 2002

(54) FOLDING MAMMOGRAPHY TABLE AND METHOD OF USE

(76) Inventor: Marianette Landis-Lowell, 935 N. Halifax Ave. #905, Daytona Beach, FL (US) 32118-3781

( * ) Notice: Subject to any disclaimer, the term of this patent is extended or adjusted under 35 U.S.C. 154(b) by 0 days.

(21) Appl. No.: 09/816,437

(22) Filed: Mar. 26, 2001

(51) Int. Cl.⁷ .................................................. A61B 6/04
(52) U.S. Cl. ...................... 378/209; 378/37; 378/208; 5/601
(58) Field of Search ........................ 378/37, 208, 209; 5/601; 600/407

(56) References Cited

U.S. PATENT DOCUMENTS

| | | | | |
|---|---|---|---|---|
| 4,015,836 A | * | 4/1977 | Redington et al. | 5/601 |
| 5,078,142 A | * | 1/1992 | Siczek et al. | 600/407 |
| 5,386,447 A | * | 1/1995 | Siczek | 378/37 |
| 5,609,152 A | * | 3/1997 | Pellegrino et al. | 600/429 |
| 5,820,552 A | * | 10/1998 | Crosby et al. | 600/407 |

* cited by examiner

Primary Examiner—Robert H. Kim
Assistant Examiner—Allen C. Ho
(74) Attorney, Agent, or Firm—Paul S. Rooy

(57) ABSTRACT

A folding mammography table having a folding thorax support hingedly attached to an upper base. The upper base is attached to a lower base by a means for adjusting the height of the upper base over the lower base. In use, the folding mammography table is sized to accommodate a mammography patient. Then the folding mammography table is folded down into the folded configuration, wherein the folding thorax support is disposed substantially horizontal. The mammography patient is then positioned on the folding mammography table, with one breast pendulously extending through a breast orifice in the folding thorax support. Gravity causes the breast to extend downwards, and X-rays are then taken of the breast. In folding mammography table embodiments incorporating two breast orifices, a breast orifice cover is used to block the breast orifice associated with a breast whose X-ray is not being taken, in order to prevent the non-X-rayed breast from interfering with the photography of the breast which is being X-rayed.

30 Claims, 5 Drawing Sheets

FOLDING MAMMOGRAPHY TABLE AND METHOD OF USE

BACKGROUND OF THE INVENTION

1. Field of the Invention

This invention relates to radiographic equipment, and in particular to a folding mammography table and method of use.

2. Background of the Invention

Mammographies, or breast X-rays, are one of the most important tools in use today to detect and fight breast cancer. Each year millions of women undergo routine mammographies in order to screen for breast cancer.

Although the X-ray cameras used during mammographies use well-proven radiographic technology which is old and well-known in the art, special equipment must be used to position the breast being X-rayed. Generally two pictures are taken: one of a breast side view, and another of a breast top view.

3. Existing Designs

The equipment currently used to position a breast being X-rayed includes a pair of parallel plates which are spaced apart sufficiently to admit the breast to be X-rayed. The breast is inserted between the plates as far as possible, and the plates are then pressed together, vice-like. The pressure is considerable, and the procedure may be painful to the patient being X-rayed. The first X-ray is then taken.

Following taking the first X-ray, the plates are separated sufficiently to permit the breast to be rotated ninety degrees, and the procedure repeated for the second X-ray. Thus, current mammography equipment is not only painful, but insult is added to injury by performing the whole painful procedure twice! Thus, it would be desirable to provide mammography breast-positioning equipment which is not uncomfortable and painful to the patient.

In addition, the entire breast is not generally photographable using the currently available parallel plates positioning devices. It would be desirable to increase the percentage of breast X-rayed, in order to increase the diagnostic effectiveness of mammographies.

SUMMARY OF THE INVENTION

Accordingly, it is an object of the present invention to provide a folding mammography table which avoids the patient discomfit and pain of the current parallel plates method. Design features allowing this object to be accomplished include a folding thorax support hingedly attached to an upper base, and breast orifices in the folding thorax support. Advantages associated with the accomplishment of this object include reduced patient pain and discomfit, and the prospect of a greater percentage of patients voluntarily submitting to periodic painless mammographies.

It is another object of the present invention to provide a folding mammography table method of use which provides X-rays covering a greater percentage of the breast. Method steps allowing this object to be accomplished include adjusting a folding mammography table for the height and proportions of the patient, folding a folding thorax support into a horizontal position, placing a breast orifice cover over a breast orifice not being used, positioning a patient with her breast pendulously hanging through the remaining breast orifice, and X-raying the breast hanging pendulously through the breast orifice. Benefits associated with the accomplishment of this object include greater X-ray coverage of the breast, and hence better diagnostic capability, as well as reduced patient discomfit and pain.

It is still another object of this invention to provide a folding mammography table and method of use which is vertically adjustable for different height and proportioned patients. Design features enabling the accomplishment of this object include a means of adjusting the height of an upper base relative to a lower base. An advantage associated with the realization of this object is increased utility of the instant invention, in order to be able to accommodate a wide variety of patients.

It is another object of the present invention to provide a folding mammography table and method of use which provides an optional means of vertically positioning patients relative to a lower base. Design features allowing this object to be accomplished include a ramp and ramp jack, or in the alternative, at least one block which the patient can stand on. A benefit associated with the accomplishment of this object is increased utility of the instant invention, in order to be able to accommodate a wide variety of patients.

It is still another object of this invention to provide a folding mammography table and method of use which provides for angular adjustment between a folding thorax support and an upper base. Design features enabling the accomplishment of this object include a hinged attachment between the folding thorax support and the upper base, and a means of changing the angle between the folding thorax support and the upper base. An advantage associated with the realization of this object is the ability to position the folding thorax support substantially horizontal, in order to be able to administer more effective and less uncomfortable mammographies.

It is another object of the present invention to provide a folding mammography table and method of use which permits the folding thorax support to be quickly and easily adjusted to a pre-determined optimal angle relative to an upper base. Design features allowing this object to be accomplished include a folding thorax support hingedly attached to an upper base, and an upper base land incorporated into the upper base. A benefit associated with the accomplishment of this object is the ability to quickly and easily position the folding thorax support into an optimum position for taking breast X-rays of a breast hanging pendulously through a breast orifice in the folding thorax support.

BRIEF DESCRIPTION OF THE DRAWINGS

The invention, together with the other objects, features, aspects and advantages thereof will be more clearly understood from the following in conjunction with the accompanying drawings.

Five sheets of drawings are provided. Sheet one contains FIG. 1. Sheet two contains FIG. 2. Sheet three contains FIGS. 3 and 4. Sheet four contains FIG. 5. Sheet five contains FIG. 6.

DETAILED DESCRIPTION OF THE PREFERRED EMBODIMENT

Figure 1:
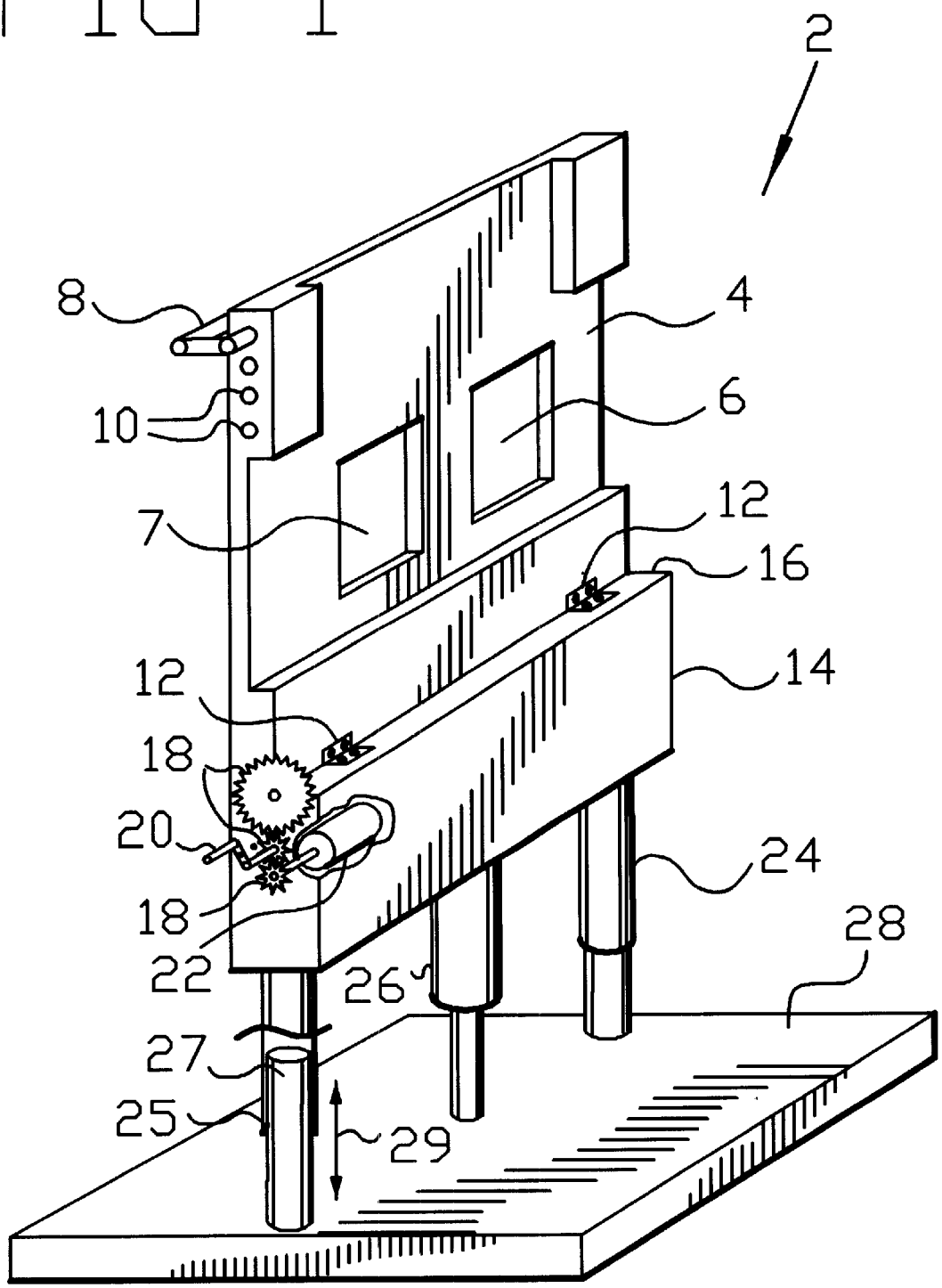
FIG. 1 is a rear quarter isometric view of a folding mammography table in the unfolded position.

Referring now to FIG. 1 we observe is a rear quarter isometric view of folding mammography table 2 with folding thorax support 4 in the unfolded position. Folding mammography table 2 comprises folding thorax support 4 attached to upper base 14 by hinges 12. Upper base 14 is adjustably attached to lower base 28 by means of guides 24 and a means of varying the height of upper base 14 relative to lower base 28. In addition, means is provided for varying the angle of folding thorax support 4 relative to upper base 14.

In FIG. 1, two means are depicted for varying the angle of folding thorax support 4 relative to upper base 14. The first means is crank 20 rotatably engaged with folding thorax support 4 by means of at least one gear 18. The second means is motor 22 rotatably engaged with folding thorax support 4 by means of at least one gear 18. Motor 22 is shown through a partial cut-away from upper base 14. By means of either crank 20 or motor 22, the angle of folding thorax support 4 relative to upper base 14 may be varied, from the unfolded position depicted in FIG. 1 to the fully folded position depicted in FIG. 2, as indicated by arrow 30 in FIG. 2. Motor 22 may be electric, hydraulic, pneumatic, or any other appropriate source of rotary motion.

Figure 5:
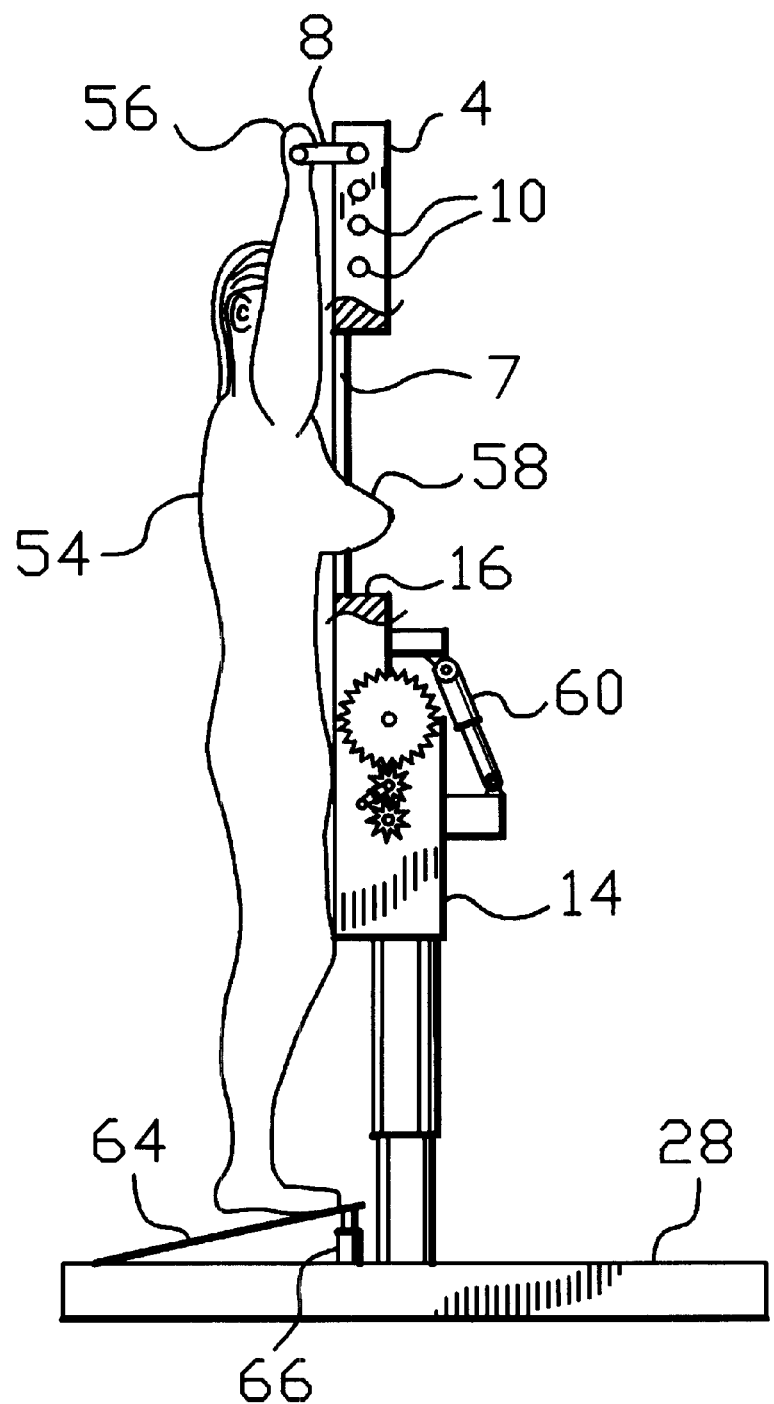
FIG. 5 is a side partial cross-sectional view of a folding mammography table being sized to fit a patient, with the folding mammography table in the unfolded position.

FIG. 5 depicts still another means of folding mammography table 2: actuator 60. Actuator 60 may be a hydraulic actuator, a pneumatic actuator, a linear electric motor, or other appropriate actuator. Actuator 60, like the other means of varying the angle of folding thorax support 4 relative to upper base 14, provides infinite adjustment of the angle of folding thorax support 4 relative to upper base 14.

Figure 4:
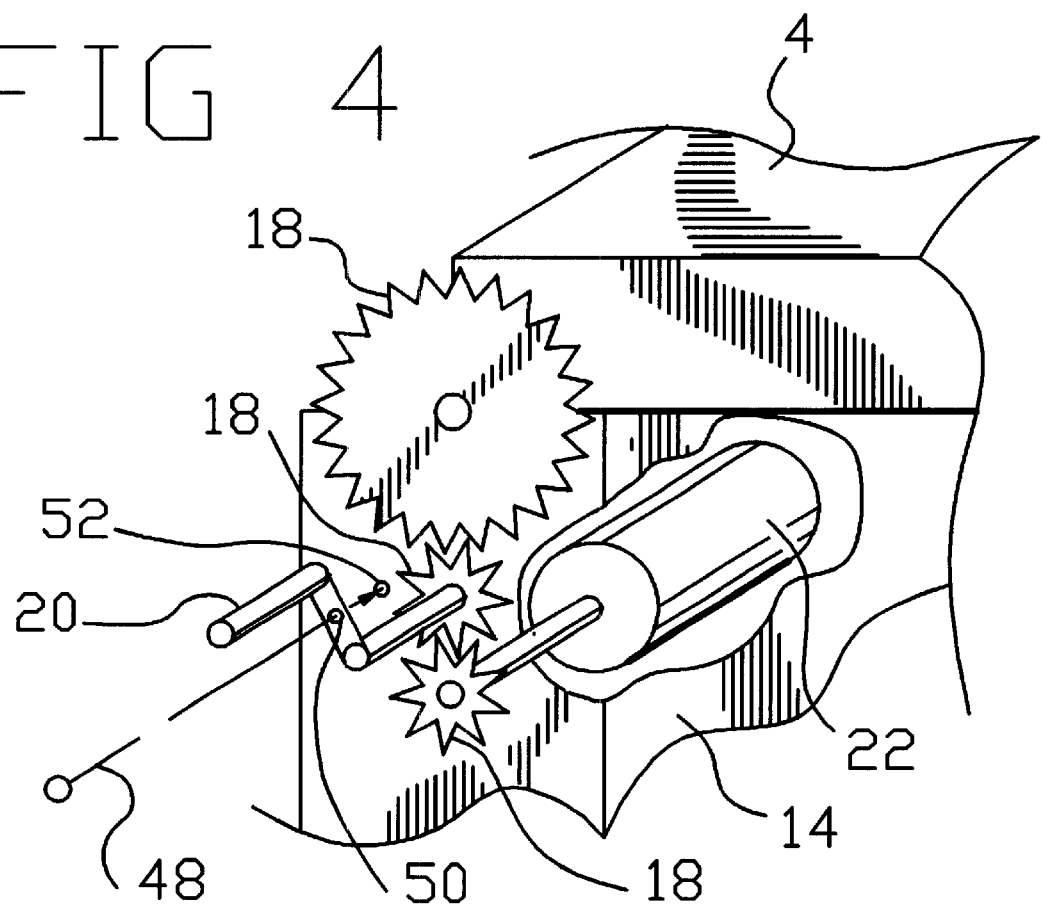
FIG. 4 is a rear quarter isometric detail view of the hinged attachment between the folding thorax support and upper base.

Means is also provided to quickly and easily set angularly immobilize folding thorax support 4 relative to upper base 14. Referring now also to FIG. 4, a rear quarter isometric detail view of the hinged attachment between folding thorax support 4 and upper base 14, one means of angularly immobilizing crank 20 relative to upper base 14 comprises upper base pin bore 52 and crank pin bore 50 sized to admit pin 48. When crank 20 has been turned sufficiently to position folding thorax support 4 at the desired angle relative to upper base 14, pin 48 is inserted through crank pin bore 50 and into upper base pin bore 52, thus locking crank 20 in place, and so also locking the angle between folding thorax support 4 and upper base 14.

Where a hydraulic, pneumatic or electrical actuator is used to vary the angle between folding thorax support 4 and upper base 14, supply and interruption of hydraulic fluid, gaseous fluid and electricity serve to angularly immobilize folding thorax support 4 relative to upper base 14.

Another means of quickly and easily fixing the angle between folding thorax support 4 and upper base 14 at a pre-determined optimal angle is upper base land 16. It has been experimentally determined that the optimal angle for pendulous mammographies at which to place folding thorax support 4 relative to vertical is 90°, with a minimum angle of 85° being desirable. By manufacturing upper base land 16 at a 90°±5° angle relative to the vertical, upper base land 16 serves as an end of travel stop for folding thorax support 4, and stops folding thorax support 4 at the optimal angle for mammographies, as shown in FIGS. 2 and 6.

Figure 2:
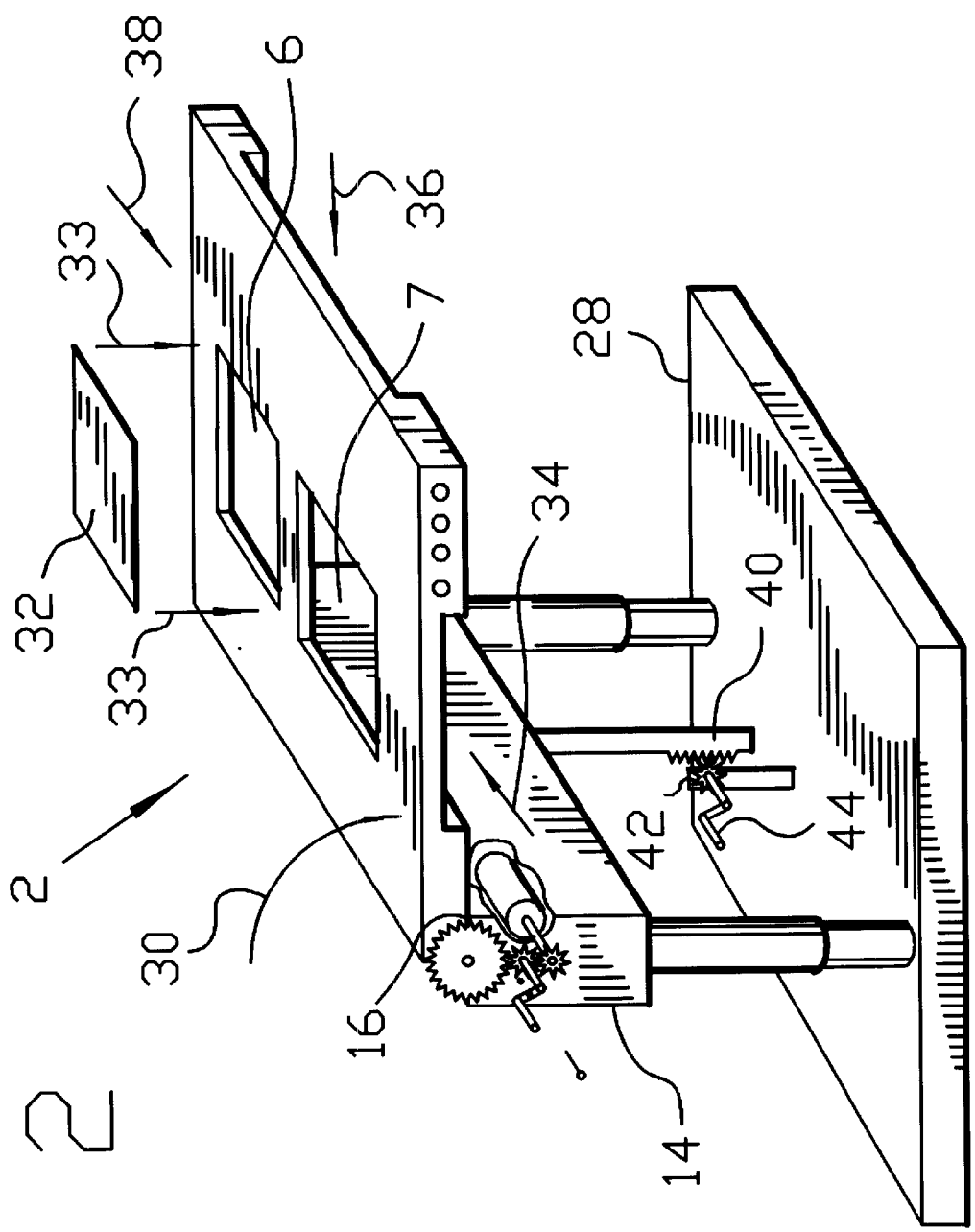
FIG. 2 is a rear quarter isometric view of a folding mammography table in the folded position.
Figure 6:
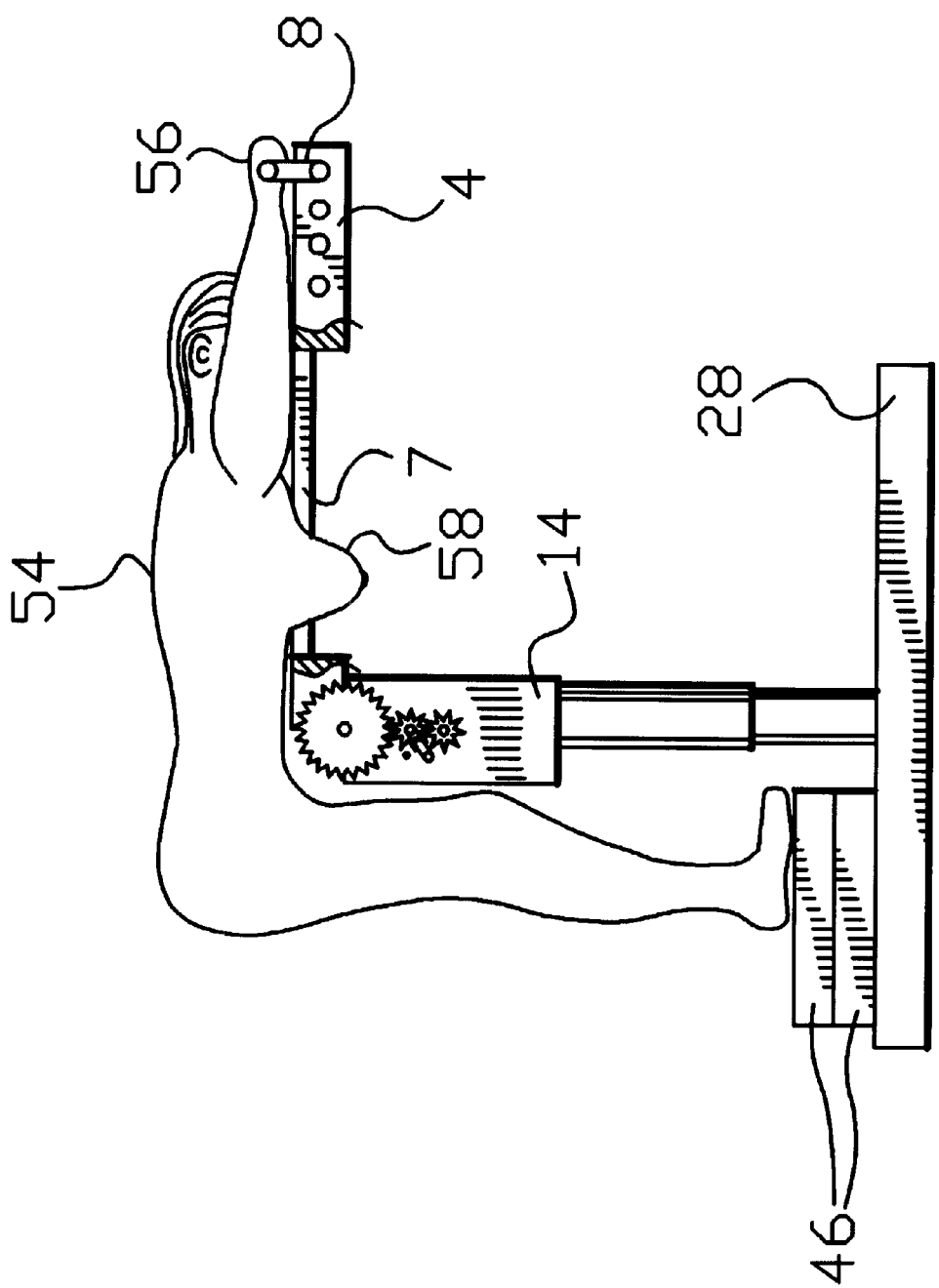
FIG. 6 is a side partial cross-sectional view of a folding mammography table in the folded position with a patient on the folding mammography table, ready to have breast X-rays taken.

Folding thorax support 4 comprises left breast orifice 6 and right breast orifice 7 sized and positioned to permit a corresponding patient breast to hang pendulously through them when folding mammography table 2 is in the folded position depicted in FIGS. 2 and 6. Breast orifice cover 32 blocks off the breast orifice not being used by the breast being X-rayed. For example, after folding mammography table 2 is sized for a given patient 54, folding mammography table 2 is folded into the position indicated in FIG. 6, breast orifice cover 32 is placed over left breast orifice 6 as indicated by arrows 33 in FIG. 2, and patient 54 is positioned on folding mammography table 2 so that right patient breast 58 hangs pendulously through right breast orifice 7. X-rays are then taken of right patient breast 58 as indicated by arrows 34, 36 and/or 38 in FIG. 2.

Then patient 54 is removed from folding mammography table 2, breast orifice cover 32 is placed over right breast orifice 7, and patient 54 is positioned on folding mammography table 2 so that the left breast of patient 54 hangs pendulously through left breast orifice 6. X-rays are then taken of the left breast of patient 54. In this fashion, breast orifice cover 32 serves to keep the breast not being X-rayed out of the way while the other breast is being X-rayed.

Figure 3:
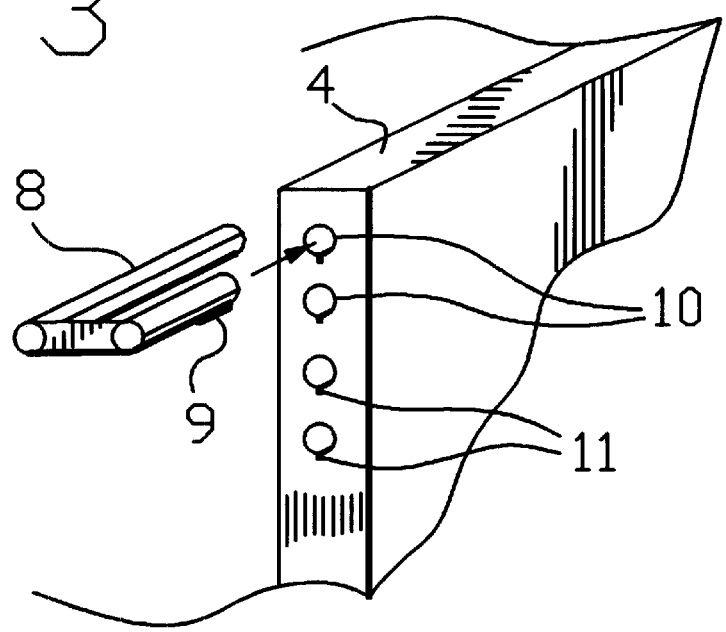
FIG. 3 is a rear quarter isometric view of the upper right corner of a folding thorax support.

Folding thorax support 4 additionally comprises hand holds 8 for the convenience of patient 54, and to aid in the vertical adjustment of upper base 14. In use, patient 54 grips hand holds 8 using patient hands 56, as depicted in FIGS. 5 and 6. Referring now also to FIG. 3, a plurality of hand hold bores 10 sized to admit hand hold 8 are provided in folding thorax support 4, in order to accommodate different height and proportioned patients 54. Each hand hold 8 comprises a hand hold key 9. Each hand hold bore 10 comprises a hand hold bore keyway 11 sized to admit hand hold key 9. When a hand hold 8 is inserted into a hand hold bore 10, so also is its corresponding hand hold key 9 inserted into the corresponding hand hold bore keyway 11, thus angularly immobilizing hand hold 8 relative to folding thorax support 4.

Folding mammography table 2 further comprises means to adjust the height of upper base 14 relative to lower base 28, in order to accommodate different sized and proportioned patients 54. Various means of adjusting the height of upper base 14 relative to lower base 28 are depicted in the different drawings. FIG. 1 shows upper base jack 26 between upper base 14 and lower base 28. Upper base jack may be a hydraulic actuator, a pneumatic actuator, a mechanical jack, a linear electric motor, or any other appropriate actuator.

One or more guides 14 may aid in holding upper base 14 vertical relative to lower base 28. FIG. 1 depicts one type of guide 24 which is effective, although any number of guide 24 configurations could be used. In FIG. 1, guide 24 comprises guide piston 27 reciprocating within guide cylinder 25, as indicated by arrow 29. Guide cylinder 25 is sized to slidably admit guide piston 27. It is contemplated to be within the scope of the instant invention to use any suitable guide, including but not limited to different shaped guide cylinders 25 and guide pistons 27, rings attached to upper base 14 sliding over guide piston 27, etc.

FIG. 2 depicts an alternate means to adjust the height of upper base 14 relative to lower base 28, in order to accommodate different sized and proportioned patients 54. The height-adjustment means depicted in FIG. 2 is rack 40 engaged with pinion 42. Pinion crank 44 is attached to pinion 42. When pinion crank 44 is rotated, so also is pinion 42, which causes rack 40 to move in reciprocal fashion relative to pinion 42. Although FIG. 2 depicts rack 40 attached to upper base 14 and pinion 42 rotatably attached to lower base 28, the reverse is contemplated to be within the scope of the instant invention: rack 40 could be attached to lower base 28, and pinion 42 could be rotatably attached to upper base 14. In addition, although FIG. 2 depicts pinion crank 44 attached to pinion 42 to provide rotary motion to pinion 42, a motor (similar to motor 22 attached to gear 18) or other circular motion source could be used, and such variations are intended to fall within the scope of this disclosure.

FIG. 5 is a side partial cross-sectional view of folding mammography table 2 being sized to fit patient 54, with the folding mammography table 2 in the unfolded position. FIG. 6 is a side partial cross-sectional view of folding mammography table 2 in the folded position with patient 54 on folding mammography table 2, ready to have breast X-rays taken. FIGS. 5 and 6 depict additional means of adjusting the vertical position of patient 54 relative to lower base 28. FIG. 5 shows ramp 64 disposed on lower base 28. Ramp jack 66 adjusts the height of an extreme of ramp 64 closest to folding mammography table 2. Ramp jack 66 may be any suitable actuator, including but not limited to a hydraulic actuator, a pneumatic actuator, a mechanical jack, a linear electric motor, or any other appropriate actuator.

FIG. 6 depicts still another means of adjusting the vertical position of patient 54 relative to lower base 28: block(s) 46. One or more block 46 may be placed under patient 54 in order to position patient 54 at the correct height relative to lower base 28.

The instant method of use for a folding mammography table comprises the following steps:

A. Positioning a folding mammography table in an unfolded position;
B. Positioning a mammography patient on a lower base, facing a folding thorax support;
C. Adjusting a height of an upper base over a lower base such that at least one said patient's breast protrudes through a breast orifice in said folding thorax support;
D. Adjusting a height of at least one hand hold above said lower base such that said patient may grasp said hand hold while standing on said lower base;
E. Removing said patient from said folding mammography table;
F. Folding said folding mammography table into a folded position, such that said folding thorax support is substantially horizontal;
G. Positioning said patient face down on said folding thorax support, with a breast to be X-rayed hanging pendulously through one said breast orifice; and
H. Taking X-rays of said breast hanging pendulously through said breast orifice.

The instant method of use for a folding mammography table may comprise the following additional steps:

A'. Adjusting a height of a ramp over said lower base in order to place a mammography patient at a correct vertical position relative to said folding thorax support; and
B'. Positioning said mammography patient on said ramp, facing a folding thorax support.
F'. Placing a breast orifice cover over a first said breast orifice corresponding to a breast which is not to be X-rayed, whereby said breast which is not to be X-rayed will not obstruct X-rays taken of said breast being X-rayed.
G'. Positioning said patient face down on said folding thorax support, with a breast to be X-rayed hanging pendulously through a second said breast orifice which is not blocked by said breast orifice cover.
I. Removing said mammography patient from said folding mammography table;
J. Moving said breast orifice cover from said first breast orifice to said second breast orifice;
K. Positioning said patient face down on said folding thorax support, with a breast to be X-rayed hanging pendulously through said first said breast orifice, which is not blocked by said breast orifice cover; and
L. Taking X-rays of said breast hanging pendulously through said first breast orifice.

While a preferred embodiment of the invention has been illustrated herein, it is to be understood that changes and variations may be made by those skilled in the art without departing from the spirit of the appending claims.

DRAWING ITEM INDEX 2 folding mammography table
4 folding thorax support
6 left breast orifice
7 right breast orifice
8 hand hold
9 hand hold key
10 hand hold bore
11 hand hold bore keyway
12 hinge
14 upper base
16 upper base land
18 gear
20 crank
22 motor
24 guide
25 guide cylinder
26 upper base jack
27 guide piston
28 lower base
29 arrow
30 arrow
32 breast orifice cover
33 arrow
34 arrow
36 arrow
38 arrow
40 rack
42 pinion
44 pinion crank
46 block
48 pin
50 crank pin bore
52 upper base pin bore
54 patient
56 patient hand
58 patient right breast
60 actuator
64 ramp
66 ramp jack

I claim:

1. A folding mammography table comprising a folding thorax support hingedly attached to an upper base, and a lower base attached to said upper base by a means for adjusting a height of said upper base over said lower base, means for varying an angle between said folding thorax support and said upper base, and at least one breast orifice in said folding thorax support.

2. The folding mammography table of claim 1 wherein said means for varying an angle between said folding thorax support and said upper base comprises a crank and at least one gear.

3. The folding mammography table of claim 2 wherein an angular position of said folding thorax support may be fixed relative to said upper base by means of a pin extending through a crank pin bore in said crank, and into an upper base pin bore in said upper base.

4. The folding mammography table of claim 1 wherein said means for varying an angle between said folding thorax support and said upper base comprises a motor and at least one gear.

5. The folding mammography table of claim 1 wherein said means for varying an angle between said folding thorax support and said upper base comprises an actuator attached at one end to said upper base, and at an opposite end to said folding thorax support.

6. The folding mammography table of claim 1 wherein said means for adjusting a height of said upper base over said lower base comprises an upper base jack engaged at one extreme with said lower base, and at an opposite extreme with said upper base.

7. The folding mammography table of claim 6 further comprising at least one guide attached at one end to said lower base, and at an opposite end to said upper base.

8. The folding mammography table of claim 7 wherein each said guide comprises a guide piston disposed within a guide cylinder, said guide cylinder being sized to slidably admit said guide piston.

9. The folding mammography table of claim 1 wherein said means for adjusting a height of said upper base over said lower base comprises a rack and pinion.

10. The folding mammography table of claim 9 further comprising a pinion crank attached to said pinion.

11. The folding mammography table of claim 9 further comprising a motor attached to said pinion.

12. The folding mammography table of claim 11 further comprising at least one guide attached at one end to said lower base, and at an opposite end to said upper base.

13. The folding mammography table of claim 12 wherein each said guide comprises a guide piston disposed within a guide cylinder, said guide cylinder being sized to slidably admit said guide piston.

14. The folding mammography table of claim 1 wherein said folding thorax support comprises at least one hand hold.

15. The folding mammography table of claim 14 further comprising means of adjusting a position of said hand hold on said folding thorax support.

16. The folding mammography table of claim 15 wherein said means of adjusting a position of said hand hold on said folding thorax support comprises a plurality of hand hold bores disposed along said folding thorax support, each said hand hold bore being sized to slidably admit an extreme of said hand hold.

17. The folding mammography table of claim 16 wherein each said hand hold further comprises a hand hold key, and wherein each said hand hold bore further comprises a hand hold bore keyway sized to admit one said hand hold key, wherein insertion of an extreme of one said hand hold into a hand hold bore simultaneously inserts one said hand hold key into a corresponding one said hand hold bore keyway, whereby said hand hold is angularly immobilized relative to said folding thorax support.

18. The folding mammography table of claim 1 wherein said upper base comprises an upper base land, whereby rotational motion of said folding thorax support is stopped at a pre-determined optimal folded position.

19. The folding mammography table of claim 18 wherein said upper base land is parallel plus or minus 5 degrees to horizontal, whereby said upper base land stops said rotational motion of said folding thorax support in a position which is parallel plus or minus 5 degrees to horizontal.

20. The folding mammography table of claim 1 further comprising means for adjusting a vertical position of a mammography patient relative to said folding thorax support.

21. The folding mammography table of claim 20 wherein said means for adjusting a vertical position of a mammography patient relative to said folding thorax support comprises a ramp disposed on said lower base, an extreme of said ramp adjacent said upper base being vertically adjustable by means of a ramp jack.

22. The folding mammography table of claim 20 wherein said means for adjusting a vertical position of a mammography patient relative to said folding thorax support comprises at least one block disposed on said lower base.

23. A folding mammography table comprising a folding thorax support hingedly attached to an upper base, and a lower base attached to said upper base by a means for adjusting a height of said upper base over said lower base, means for varying an angle between said folding thorax support and said upper base, and two breast orifices in said folding thorax support.

24. The folding mammography table of claim 23 further comprising at least one hand hold removably attached to said folding thorax support, and means for adjusting a position of said hand hold along said folding thorax support.

25. The folding mammography table of claim 24 further comprising means of adjusting a vertical position of a mammography patient relative to said folding thorax.

26. The folding mammography table of claim 23 wherein said upper base further comprises an upper base land, whereby rotational motion of said folding thorax support is stopped at a position which is substantially horizontal.

27. A method of use for a folding mammography table, said folding mammography table comprising a folding thorax support hingedly attached to an upper base, and a lower base attached to said upper base by a means for adjusting a height of said upper base over said lower base, means for varying an angle between said folding thorax support and said upper base, and at least one breast orifice in said folding thorax support, said method comprising the steps of:

A. Positioning said folding mammography table in an unfolded position;

B. Positioning a mammography patient on said lower base, facing said folding thorax support;

C. Adjusting a height of said folding thorax support over said lower base such that at least one said patient's breast protrudes through one said breast orifice;

D. Removing said patient from said folding mammography table;

E. Folding said folding mammography table into a folded position, such that said folding thorax support is substantially horizontal;

F. Positioning said patient face down on said folding thorax support, with a breast to be X-rayed hanging pendulously through one said breast orifice; and G. Taking X-rays of said breast hanging pendulously through said breast orifice.

28. The method of use for said folding mammography table of claim 27 wherein said folding mammography table comprises at least one hand hold, and wherein said method comprises the further step of adjusting a height of at least one hand hold above said lower base such that said patient may grasp said hand hold while standing on said lower base.

29. The method of use for said folding mammography table of claim 27 wherein said folding mammography table further comprises means for adjusting a vertical position of a mammography patient relative to said folding thorax support, and wherein said method comprises the further step of setting a vertical position of a mammography patient relative to said folding thorax support.

30. A method of use for a folding mammography table, said folding mammography table comprising a folding thorax support hingedly attached to an upper base, and a lower base attached to said upper base by a means for adjusting a height of said upper base over said lower base, means for varying an angle between said folding thorax support and said upper base, a first and second breast orifice in said folding thorax support, and a breast orifice cover sized to cover one said breast orifice, said method comprising the steps of:

A. Positioning said folding mammography table in an unfolded position;

B. Positioning a mammography patient on said lower base, facing said folding thorax support;

C. Adjusting a height of said folding thorax support over said lower base such that at least one said patient's breast protrudes through one said breast orifice;

D. Removing said patient from said folding mammography table;

E. Folding said folding mammography table into a folded position, such that said folding thorax support is substantially horizontal;

F. Placing a breast orifice cover over said first breast orifice corresponding to a first patient breast, which is not to be X-rayed, whereby said first patient breast will not obstruct X-rays taken of a second patient breast;

G. Positioning said patient face down on said folding thorax support, with said second patient breast hanging pendulously through said second breast orifice, which is not blocked by said breast orifice cover;

H. Taking X-rays of said second patient breast hanging pendulously through said second breast orifice;

I. Removing said mammography patient from said folding mammography table;

J. Moving said breast orifice cover from said first breast orifice to said second breast orifice;

K. Positioning said patient face down on said folding thorax support, with said first patient breast hanging pendulously through said first said breast orifice, which is not blocked by said breast orifice cover; and L. Taking X-rays of said first patient breast which is hanging pendulously through said first breast orifice.

* * * * *